(12) United States Patent
Galande et al.

(10) Patent No.: US 7,604,980 B2
(45) Date of Patent: Oct. 20, 2009

(54) PROTEIN EXPRESSION SYSTEM

(75) Inventors: Sanjeev Galande, Pune (IN); Prabhat K. Purbey, Pune (IN); Peter C. Jayakumar, Pune (IN); Milind S. Patole, Pune (IN)

(73) Assignee: National Centre for Cell Science, Pune (IN)

( * ) Notice: Subject to any disclaimer, the term of this patent is extended or adjusted under 35 U.S.C. 154(b) by 176 days.

(21) Appl. No.: 11/347,717

(22) Filed: Feb. 2, 2006

(65) Prior Publication Data

US 2007/0037251 A1    Feb. 15, 2007

(51) Int. Cl.
*C12N 1/20* (2006.01)
*C12N 15/00* (2006.01)

(52) U.S. Cl. .................. 435/252.3; 536/23.2; 435/226; 435/320.1

(58) Field of Classification Search ................. 435/69.1, 435/226, 252.3, 320.1; 536/23.2
See application file for complete search history.

(56) References Cited

U.S. PATENT DOCUMENTS 7,365,185 B2 *   4/2008   Boukharov et al. ........ 536/24.1

\* cited by examiner

*Primary Examiner*—Tekchand Saidha
(74) *Attorney, Agent, or Firm*—Edwards Angell Palmer & Dodge LLP; Jonathan M. Sparks (57) ABSTRACT

The present invention relates to proteomics, especially downstream processing of proteins. The present invention also relates to novel expression cassettes having unique cleavage sites for efficient removal of purification tags. The invention further provides expression systems and a methods for purifying and isolating proteins.

10 Claims, 3 Drawing Sheets

FIG. 1A
Scheme for modification of pGEX 4T2 into pC6-2

```
Leu Val Pro Arg Gly Ser Pro Gly ILeu Pro Gly Ser Tyr Arg
CTG GTT CCG CGT GGA TCC CCA GGA ATT CCC GGG TCG ACT CGA
GAC CAA GGC GCA CCT AGG GGT CCT TAA GGG CCC AGC TGA GCT
         BamHI Site          (BamHI digestion + CIP treatment)
```

FIG. 1B

```
                          GA TCC CCA GGA ATT CCC GGG TCG ACT CGA
CTG GTT CCG CGT G            GGGT CCT TAA GGG CCC AGC TGA GCT
GAC CAA GGC GCA CCT AG
```

(Ligation of Phosphorylated, annealed primer)

```
    GAT CTG TTG AAA TGG ATG
        AC AAC TTT ACC TAC CTA G
```

```
Leu Val Pro Arg Gly Ser Val Glu Met Asp Gly Ser Pro Gly Ile Pro Gly Ser Tyr Arg
CTG GTT CCG CGT GGA TCT GTT GAA ATG GAT GGA TCC CCA GGA ATT CCC GGG TCG ACT CGA
GAC CAA GGC GCA CCT AGA CAA CTT TAC CTA CCT AGG GGT CCT TAA GGG CCC AGC TGA GCT
                                     New BamHI Site
```

PROTEIN EXPRESSION SYSTEM

RELATED APPLICATIONS

This application claims priority to Indian Patent Application No. 105/MUM/2005, filed Feb. 2, 2005, entitled "A Novel Protein Expression System" and is hereby incorporated by reference in its entirety.

FIELD OF THE INVENTION

The present invention relates to the field of proteomics, especially to downstream processing of proteins. The present invention relates to a novel expression cassette comprising a unique cleavage site useful for efficient removal of purification tag. The invention also provides an expression system and a method for purifying and isolating proteins employing the expression cassette of the invention.

BACKGROUND OF THE INVENTION

The traditional method for synthesis of proteins is to produce them in a laboratory or isolate them from natural sources. One major disadvantage of this process is that the desired protein is generated in small amounts and the task is laborious. With technological advances, especially in molecular biology, several important tools for protein synthesis have now become available. One such tool is the deployment of a host system such as a bacterium into which the gene encoding the protein of interest is cloned and culturing of the host system yields the protein of interest in large quantities.

While such a system marks a significant advance over traditional methods of protein production, this technique suffers from the disadvantage that the protein produced by the host requires extensive downstream processing of the cell lysate, which is time consuming and expensive. Further, such processing could cause denaturation of the protein or cause loss of activity of the protein isolated which defeats the idea of obtaining protein in active form.

Accordingly, one of the strategies employed in protein purification is to prepare a fusion protein i.e. a protein of interest fused to another protein. The "other" protein in the fusion protein may be a purification "tag" or a purification region. The purification "tag" or region is a protein, which although fused to the protein of interest enables the protein of interest to be purified to near homogeneity in a one step purification procedure using a resin with affinity for the tag. When the cell lysate is passed over a column, the tag binds to the resin column and along with it retains the protein of interest. All other proteins from the lysate do not bind and are eliminated in the flow-through of the column or the washes. The column-bound proteins are then released by passing a solution containing a small molecular weight competitor for the affinity tag that displaces the fusion protein.

The Glutathione-5-transferase (GST) fusion protein expression system is a popular system used for high level expression and subsequent purification of proteins in *Escherichia coli*. GST fusion proteins may be eluted competitively by using reduced glutathione without affecting the antigenicity and functional activity of recombinant proteins.

After a chimeric molecule (fusion protein) has been isolated, it is necessary to remove the "tag" prior to the use of the expressed protein of interest. "Tag" removal is typically achieved by use of specific proteases such as thrombin or factor Xa.

Although these proteases are considered specific for cleavage at the inserted cleavage site, proteolysis may frequently occur at other site(s) in the protein of interest. Additionally, relatively extended incubation times (4-16 h) are required for efficient cleavage by the two proteases listed above. As a result, there could be loss in amount of proteins obtained or labile proteins may lose their activity during such prolonged incubation periods. Further, in the GST-fusion protein system, the protease used for removal of GST-tag remains as a contaminant in the protein preparation.

To overcome the said problems in the art, it is desirable to provide an expression system comprising a cleavage site which is rare in naturally occurring proteins and which system can yield a cleaved product in a relatively short period. It is also desirable to provide an expression system that allows removal of the protease after cleavage of the "Tag".

OBJECTS OF THE INVENTION

The main objective of the invention is to provide a protein expression cassette comprising a cleavage site which is rare in naturally occurring proteins and also for obtaining proteins within a short period and in high purity.

DESCRIPTION OF THE INVENTION

Accordingly, in one aspect, the invention provides a novel expression cassette comprising in operative linkage, a sequence encoding for a fusion protein consisting of a protein of interest, said protein having no internal cleavage site for a caspase and fused to a purification tag; and an oligonucleotide including a recognition sequence for caspase.

The caspase employed in the invention may be selected from a member of the caspase family such as caspase 6, caspase 3, caspase 7, or caspase 11. Usually, the cleavage of proteins occurs after the aspartate site in the construct. The cleavage site employed would depend upon the proteins used. In case of caspase 6, the cleavage site may be V-E-M-D (SEQ ID NO: 1) i.e. Valine-glutamic acid-methionine-aspartic acid (SEQ ID NO: 1) or val-glu met-asp (SEQ ID NO: 1) or V-E-I-D (SEQ ID NO: 2). The said cleavage recognition site is highly specific for caspase-6. The said caspase-6-cleavage site is cleaves only at the said VEMD (SEQ ID NO: 1) site or VEID (SEQ ID NO: 2) and not anywhere else, thus allowing greater amount of proteins to be obtained at the end of purification procedure.

Although any of the caspases may be used for protein purification, several advantages are found in using caspase-6 in the expression system of the invention since the purity and amount of the protein recovered is very high. Further, the caspase-6 cleavage reaction is very quick since caspase-6 can cleave upto 90% of the fusion protein in 10 minutes. Hence, greater amount of protein is obtained within short duration and the activity of the protein is also not affected.

The fusion protein in the cassette of the invention may comprise any protein of interest as long as it has no internal cleavage site for caspase-6. Examples of such a protein are p53 (a tumor suppressor protein), domains of SATB1 (special AT-rich binding protein), PARP, cMyb, cMyc, Ikaros, HDAC1, etc.

The purification "tag" may be a protein used in purification procedures and may be selected from poly/hexahistidine (6×His tag disclosed as SEQ ID NO 18), a glutathione-5-transgerase tag derived from the patasite helminth *schistosoma* japonica or derived from other species such as mammals, T7 tag, S tag, HSV tag, Trx (Thioredoxin) tag, CBD (Cellulose binding domain) tag, MBD (maltose binding domain) tag, CBD (Chitin binding domain) tag, GFP (Green fluorescent protein) tag, RFP (Red fluorescent) tag etc.

Thus, any protein of interest may be fused to GST or any other tag listed above and recovered employing the expression system of the invention.

Further, the expression cassette comprises a recognition site for the protease i.e. the caspase in question. The said site may be one comprising an aspartase. If for instance, the caspase is caspase-6, the said site may comprise the amino acid residues V-E-M-D (SEQ ID NO: 1) i.e. Valine-glutamic acid-methionine-asparatic acid (SEQ ID NO: 1) or V-E-I-D (SEQ ID NO: 2); but including an aspartic acid residue. The aforementioned components of the expression cassette may be operatively linked in proper reading frame. Preferably, if the caspase is caspase-6 recognition site may be located downstream or upstream of the protein of interest if the fusion tag is at N or C terminal respectively.

Preferably, the expression cassette may be conveniently expressed using any expression vector selected from the pGEX family or any such vector capable of expressing a fusion protein. Preferably, the vector is selected from pGEX-1λT, pGEX-2T, pGEX-2TK, pGEX-4T-1, pGEX-4T-2, pGEX-4T-3, and other vectors in the pGEX series and also the pET series. Many other vectors with design similar to those mentioned above also can be used.

The invention also includes a host cell comprising the expression vector containing a cleavage recognition site for the caspase for protein expression.

In another aspect, the invention provides a kit comprising the expression cassette of the invention and other ingredients such as a Caspase cleavage buffer (20 mM PIPES pH 7.2, 100 mM NaCl, 10 mM DTT, 1 mM EDTA, 0.1% CHAPS, 10% sucrose,) and caspase enzyme.

In yet another aspect, the invention provides a method for producing an amino acid of interest, comprising the steps of:
a) providing an expression vector comprising an expression cassette including a sequence encoding for a fusion protein including a purification tag and an oligonucleotide for recognition of a caspase cleavage site,
b) transforming a host cell with the expression vector,
c) culturing a host cell under conditions whereby the fusion protein is expressed in recoverable amount,
d) lysing the host cell to obtain a lysate,
e) performing an affinity purification step by eluting the lysate with a buffer including containing caspase and incubating on a resin column for 15 minutes to 4 hours to release the protein of interest, and collecting the eluate and isolating the protein of interest.

In the above method, the host cell may be a cell suited for expression of fusion proteins such as *E. coli*, yeast, insect cells, and mammalian cells can be used but a new cassette would have to be constructed where promoter should correspond to the host for example a plo baculovirus promoter based vector for insect cell expression, a CMV promoter based vector for the mammalian cell expression. The buffer as recited is a cleavage buffer and comprises Tris, NaCl, $CaCl_2$ and caspase-6. The resin in the column may be a Glutathione-Sepharose-matrix. Finally, after elution, the protein of interest may be isolated and characterised by methods known in the art.

In the prior art over expression of certain protein has been described. The inventors of the present application, during one of the routine experiments of protein purification had employed a caspase recognition site. To their utter surprise, the inventors found that the cleavage of the fusion protein occurred in a very short period of less than 5-10 minutes. The inventors were even more surprised to find that after mass spectroscopy studies, the protein recovered was fully intact.

The inventors investigated this finding in great detail and presuming that proteolysis by a caspase could yield such a pure product, proceeded to perform similar experiments of protein purification by cloning caspase recognition sites for caspase-6, caspase-3, caspase-7, caspase-11, caspase-13 and other activator caspases. As a result of these experiments, the inventors found surprisingly that intact proteins are obtained within a short period of less than 10 minutes when any of these caspases are used. The results with caspase-6 recognition site cloned into vector were better than currently used processes.

From the above it emerges that thus, hitherto it was unknown that deployment of a caspase recognition site in an expression system could be efficiently used to cleave and recover any protein of interest from a fusion protein within a relatively short period of time. It was also unknown that the protein of interest could be recovered free from contaminating proteins. Yet another advantage of the system is that availability of the vectors of the invention would facilitate expression and purification of a large number of proteins that otherwise contain internal cleavage sites for various proteases (such as Thrombin and factor Xa) which are typically used for removal of the fusion tag.

Additionally, the cleavage by a caspase such as caspase-6 is extremely substrate specific and it cleaves only at certain specific sites such as V-E-M-D (SEQ ID NO: 1) and not anywhere else; hence no protein is lost in proteolysis and the amount of protein recovered is greater than in the prior art. Further, a lot of time is saved in protein purification as compared to the prior art since the cleavage reaction is very fast and can cleave up to 90% of fusion protein in 10 minutes when the enzyme: substrate concentration is 1:500 at 37° C. As a result, the proteins are exposed to high temperature for a minimal period and therefore their activity at the end of the process is unaffected, which is a great advantage as compared to prior art processes using thrombin which require several hours (4-24 h) of incubation under identical conditions. The expression system of the present invention is versatile and can be used for most proteins as opposed to other executioner caspases or thrombin or commercially available proteases. Yet another advantage of the invention is that the protease can be removed from eluted protein simply by passing through an affinity column whereas in the prior art removal of protease is difficult or expensive, for example when anti-thrombin affinity column is used.

The expression cassette, expression system, its construction and other aspects of the invention are illustrated by the following examples which should not be construed as limitations on the inventive concept thereof:

MATERIALS

Caspase-6: The nucleotide sequence of caspase-6, the polypeptide as well as its splice variants are disclosed in U.S. Pat. No. 5,985,640 which is incorporated here in its entirety.

Vectors: The vectors employed in the present invention belong to pGEX family. The sequence and other particulars of these vectors are accessible at Gen Bank database. In particular, vector pGEX-4T2 is accessible at accession No. 413854. These vectors may also be purchased from Amersham Biosciences.

*E. Coli* strain DH5α: These are strains of bacterial cells used for transformation and may be purchased from GATC, konstanz. *E. Coli* XL1 blue cells are also commercially available cells used for protein expression. They may be purchased from Stratagene.

Example 1

To demonstrate the efficiency of the expression system of the invention as compared to prior out systems, a vector pGEX-4T-2 was manipulated to engineer a site for recognition of caspase-6 downstream a thrombin cleavage site.

Figures 1A, 1B, 1C:
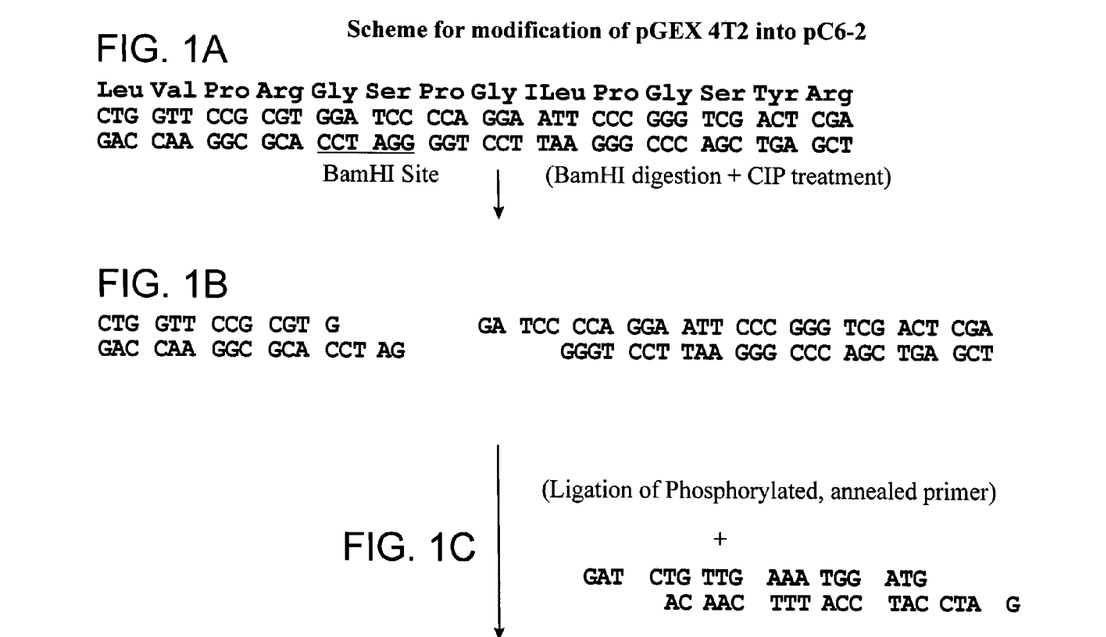
FIGS. 1A-D. depict the construction of pC6-2 vector from pGEX 4T2
Figure 1D:
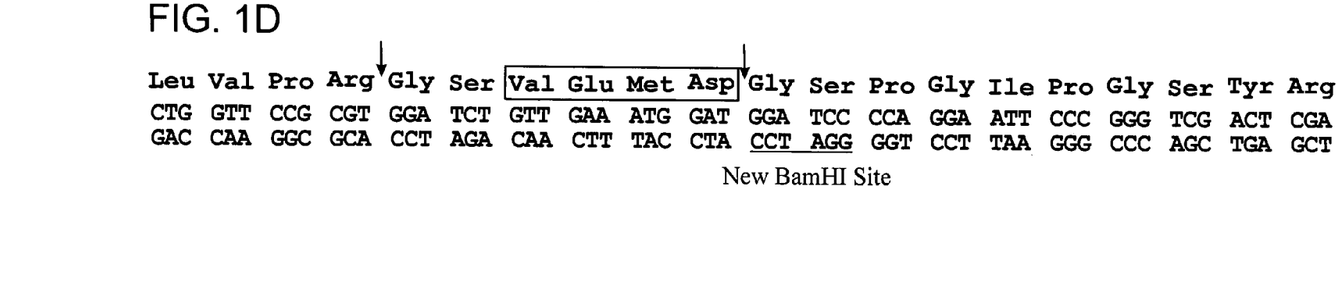
Figure 1E:
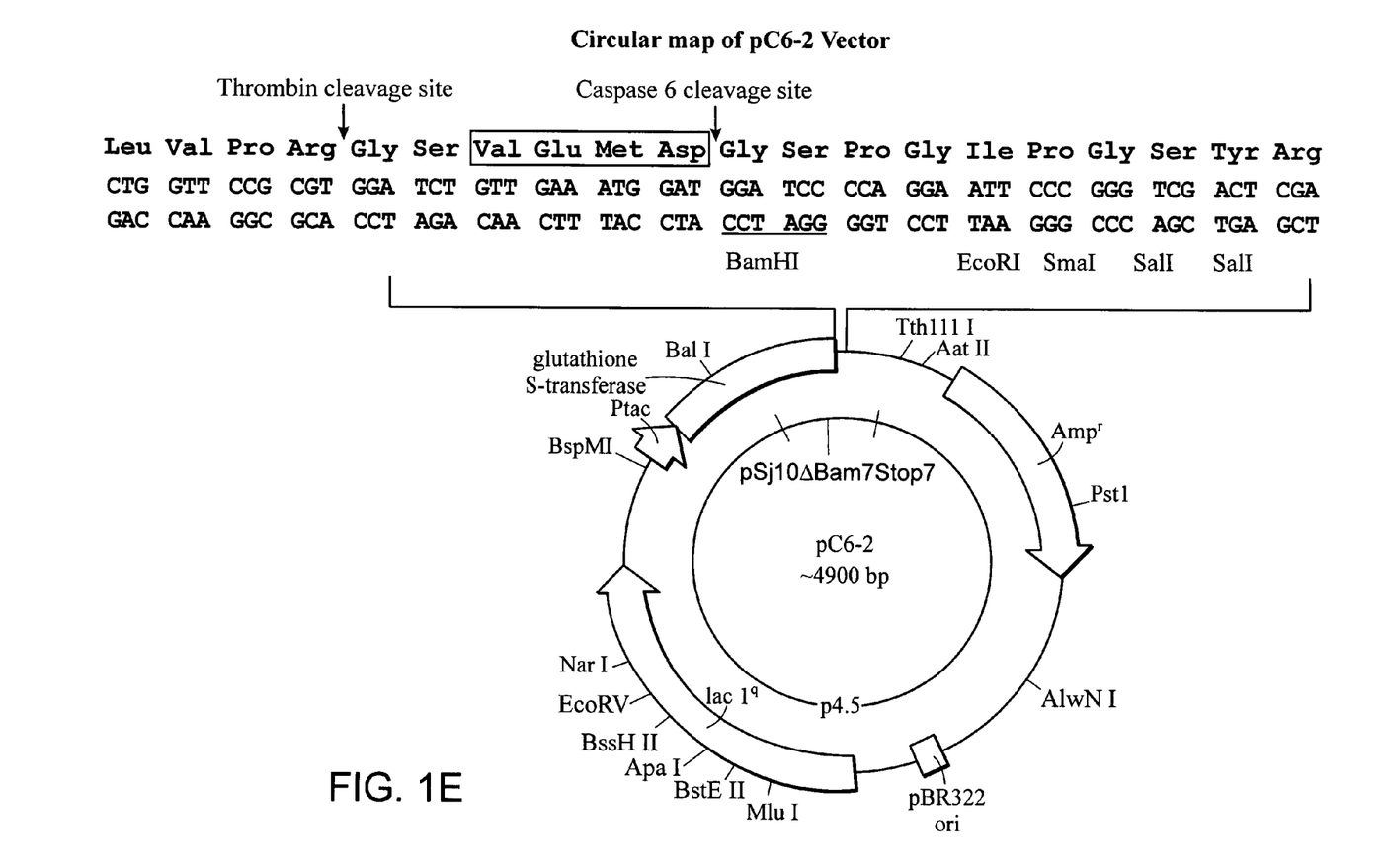
FIG. 1E depicts the plasmid map of pC6-2.

Two oligonucleotides casp6-F and casp6-R were designed (Table 1) which upon annealing generated a short synthetic DNA fragment. This fragment included the recognition site for caspase-6 and preserved a downstream BamHI site upon ligation into BamHI digested pGEX-4T-2 expression vector. The codon usage in *E. coli* was considered while designing the oligonucleotide (www.kazusa.or.jp/codon/E.html). The annealed oligonucleotides were phosphorylated at 5' ends and ligated with BamHI digested, dephosphorylated pGEX-4T-2 vector that was then used to transform competent *E. coli* strain DH5-alpha cells. Transformants were screened by polymerase chain reaction (PCR) using the casp6-F primer and a pGEX-4T2 vector specific reverse primer, pGEX-3' (Table 1). After confirmation of the sequence of MCS and caspase-6 site we named the modified pGEX-4T-2 vector as pC6-2 vector (FIG. 1).

We subcloned the cDNA encoding the N-terminal region of special AT-rich binding protein 1 (SATB1) into the pC6-2 vector (pC6-2-PDZ) to demonstrate the utility of our vector/caspase-6 system in the expression and purification of proteins with internal thrombin cleavage sites. SATB1 is a T-cell specific nuclear matrix attachment region (MAR)—binding protein which contains an N-terminal PDZ like domain essential for its dimerization and DNA binding activity (7). Our initial attempt at purification of this domain (amino acids 1-204) by expressing as GST fusion protein and then cleaving it using thrombin was unsuccessful due to presence of an internal thrombin cleavage site. For cloning into the pC6-2 vector, the N-terminal region of SATB1 encoding 204 amino acids was amplified by using 5'BamHI-F and 204BamHI-R primer pair (Table 1) from full length human SATB1 cDNA cloned in pBluescript (Stratagene) as template (pAT1146) (8) under appropriate PCR conditions. After digestion of PCR product with BamHI it was ligated into BamHI digested and dephosphorylated pC6-2 vector. The orientation of the fragment was confirmed by automated DNA sequencing. We also subcloned cDNA encoding the N-terminal region of p53 into the pC6-2 vector, which unlike SATB1, is a non-native substrate of caspase-6 and bears no internal thrombin cleavage sites. This N-terminal domain of P53 is reported to be a substrate for the ATM kinase (9). The 303 bp BamHI-EcoRI DNA fragment of pGEX-2T-p53 encoding N-terminal 101 amino acid residues of p53 was subcloned into the BamHI-EcoRI double digested pC6-2 vector.

Transformation and Protein Production:

The hexahistidine ($his_6$) (SEQ ID NO: 18) tag fused with the recombinant caspase-6 could be also utilized for its removal from the protein of interest by passing through a nickel affinity column. The constructs pGEX-2T-p53, pC6-2-PDZ, pC6-2-p53 and pC6-2 were used to transform competent *E. coli* strain XL1 blue cells (Stratagene). One colony from each were grown for 16 h in 5 ml LB media supplemented with 50 µg/ml of ampicillin and then next day 1 ml of culture was inoculated into 250 ml of prewarmed LB media supplemented with 50 µg/ml of ampicillin. Induction of protein expression was carried out at $A_{600}$=0.8 by adding IPTG at 0.5 mM. Cells were grown for 3 h and harvested.

Processing and Obtaining Protein of Interest:

The cells above were harvested by centrifugation and resuspended in buffer A (50 mM Tris HCl, 150 mM NaCl, 0.2% triton X100 and 1 mM DTT). Soluble cell lysate was then prepared by sonication followed by centrifugation at 13000 rpm for 20 min. The soluble supernatant and insoluble pellets were checked for the presence of fusion protein. The GSTC6, GST-p53 and GSTC6-p53 proteins were found in soluble fraction whereas the GSTC6-PDZ was present in insoluble fraction. The level of expression of GSTC6, GST-p53 and GSTC6-p53 was in the range of 4-5 mg/L whereas that of GSTC6-PDZ was 7-8 mg/L. The GSTC6-PDZ was solubilized in 0.3% sarcosyl followed by extensive dialysis in buffer A. Approximately 70% of the protein was refolded and solubilized in the buffer A whereas remaining 30% precipitated as aggregates.

Affinity Purification:

Two hundred µl Glutathione Sepharose beads (Amersham Biosciences) were incubated separately with 4 ml each of sarcosyl solubilized and dialyzed GST-PDZ (0.3 mg) and soluble lysates of GSTC6 (0.2 mg), GST-p53 (0.2 mg), and GSTC6-p53 (0.2 mg) in separate tubes. Sample and glutathione Sepharose beads were incubated for 30 min at 4° C. with proper mixing. The protein-bound beads were packed separately in 3×2 ml econo columns (BioRad) and washed three times with buffer A. One column of each sample was used to elute the GST fusion proteins by passing 200 µl of 10 mM reduced glutathione (Sigma) whereas second and third columns were used to perform caspase 6 and thrombin (Sigma) cleavage respectively.

In another separate experiment, $His_6$-tagged caspase-6 (6×His tag disclosed as SEQ ID NO:18) was expressed and purified essentially as described above (6), except that the $his_6$-tagged caspase-6 (6×His tag disclosed as SEQ ID NO:18) was passed twice over the nickel affinity column (Amersham Biosciences) to minimize contaminants.

Figure 2A:
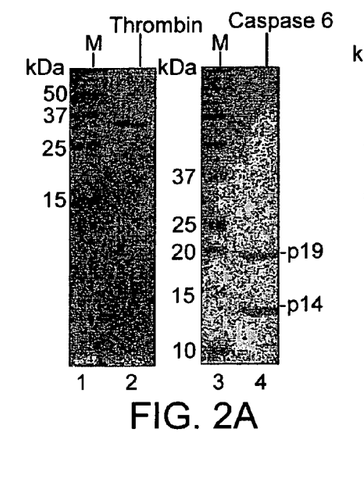
FIGS. 2A-D. demonstrate that the cleavage of column-bound fusion proteins by caspase 6 releases proteins free of the GST tag more efficiently as compared to thrombin.

Assay & Protein Analysis:

The processed and purified caspase-6 has two subunits (FIG. 2A, lane 4). Thrombin used for cleavage originated from human plasma (Sigma, T4393). To compare the homogeneity of thrombin preparation with caspase-6, we resolved 0.5 µg of thrombin on 18% SDS-PAGE and detected by staining with coomassie blue. We observed a single protein band of ~33 kDa (FIG. 2A, lane 2) and no other detectable protein contaminants in this commercial preparation, suggesting that the purity of the two proteases used in this study is comparable. Different molar ratios of purified caspase-6 enzyme to substrate GSTC6-PDZ (ranging from 1:50 to 1:1000) were employed to optimize the maximum cleavage at minimum enzyme concentration in vitro. We found that 1:500 molar ratio of caspase 6: substrate (GST-PDZ) was most optimal for both the proteins tested. Higher amounts of enzyme achieved cleavage in shorter time without affecting the specificity of cleavage.

To confirm that the cleavage can be efficiently performed on column, 50 µg of glutathione Sepharose (Amersham Biosciences) bound GSTC6-PDZ, GSTC6-p53 and GST-p53 proteins were cleaved by incubating 100 ng of recombinant caspase 6 for 30 min in 100 µl of caspase buffer (20 mM pipes, 100 mM NaCl, 10 mM DTT, 1 mM EDTA, 0.1% Chaps, 10% Sucrose, pH 7.2) at room temperature. Similarly 50 μg of glutathione Sepharose (Amersham Biosciences) bound GSTC6-PDZ, GSTC6-p53 and GST-p53 proteins were cleaved by incubating with 1 unit (~1 μg) of thrombin in thrombin cleavage buffer (50 mM Tris, 150 mM NaCl, 2.5 mM CaCl$_2$, pH 8.0) at room temperature for 3 h.

The cleaved product was eluted using additional 100 μl of respective cleavage buffers. Beads were then washed twice with buffer A, and the column bound GST was eluted using 10 mM reduced glutathione in buffer A. The cleavage products or eluted proteins were analyzed by SDS-PAGE followed by Coomassie staining (FIG. 2).

Figure 2B:
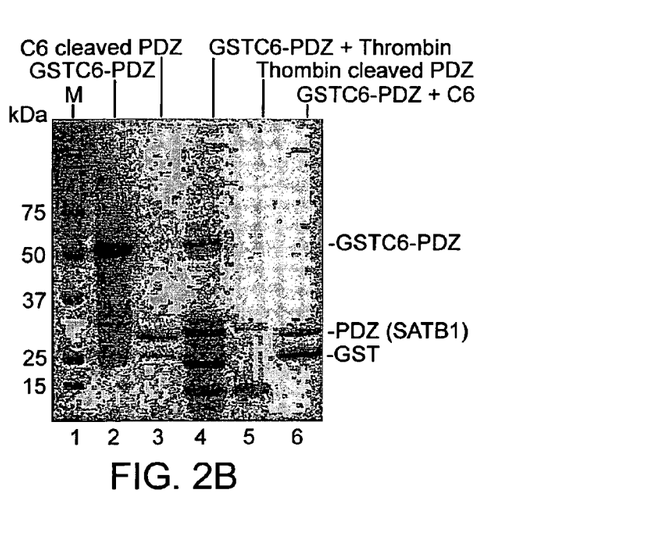
Figure 2C:
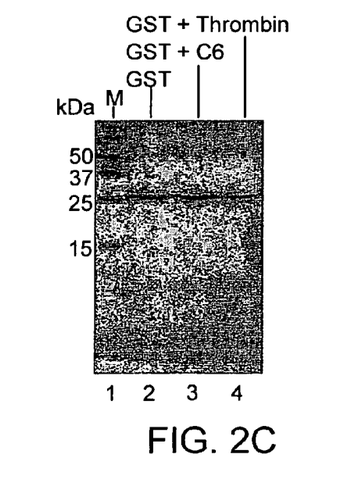
Figure 2D:
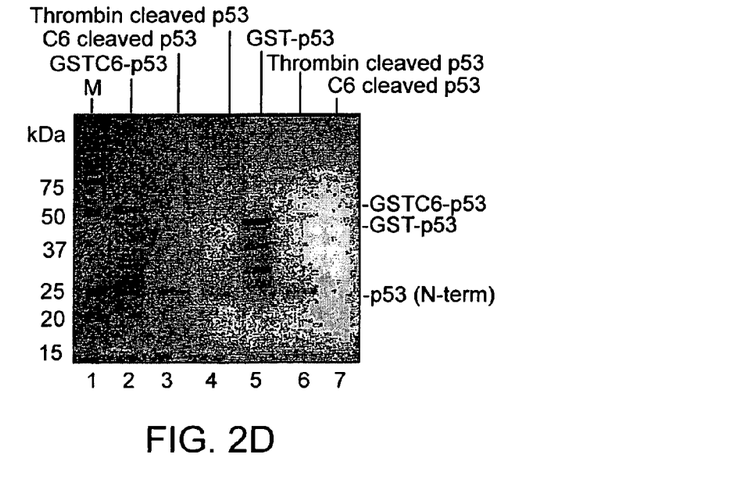

Results:

The inventors observed that the N-terminal domains of both SATB1 and p53 migrated anomalously on SDS-PAGE with or without the GST tag. The column-bound GSTC6-PDZ, GSTC6-p53 and GST-p53 fusion proteins were cleaved with caspase 6 (FIG. 2B, lane 3; FIG. 2D, lane 3, and FIG. 2D, lane 7 respectively) and thrombin (FIG. 2B, lane 5; FIG. 2D, lane 4, FIG. 2D, lane 6 respectively). Caspase 6 efficiently cleaved the GSTC6-PDZ (FIG. 2B, lane 3) and GSTC6-p53 (FIG. 2D, lane 3) on column, whereas thrombin cleaved the GSTC6-PDZ (FIG. 2B, lane 4), GSTC6-p53 (FIG. 2D, lane 4) and GST-p53 (FIG. 2D, lane 6) less efficiently as judged by the retention of the bands corresponding to full length fusion proteins. Moreover, cleavage of the PDZ-like domain of SATB1 using thrombin predominantly generated low molecular weight products (FIG. 2B, lane 5) due to presence of an internal thrombin cleavage site.

To compare the specificity of cleavage we incubated the purified GSTC6-PDZ fusion protein separately with thrombin or caspase-6 in vitro. Cleavage of GSTC6-PDZ by caspase-6 was highly efficient and generated only two species as expected (corresponding to PDZ and GST proteins, FIG. 2B, lane 6). However, cleavage of GSTC6-PDZ by thrombin was incomplete and generated additional low molecular weight products (FIG. 2B, lane 4). Amino acid sequence analysis of the N-terminal region of SATB1 using online ExPASy tool (au.expasy.org/tools/peptidecutter/) confirmed the presence of internal thrombin cleavable site. To rule out any non-specific protease activity and that caspase-6 or thrombin can not cleave at any other sites, 2.5 .mu.g of purified GST was incubated in caspase buffer without addition of any enzyme or with the addition of 15 .mu.g of caspase-6 in a total of 50 .mu.l reaction. Independently, 2.5 .mu.g of pure GST was also incubated with 0.1 unit of thrombin in total of 50 .mu.l thrombin cleavage buffer.

Additionally, glutathione Sepharose-bound GST-p53 was incubated with caspase-6 in caspase buffer. GST remained intact even after prolonged incubation of 16 h at 37° C. with caspase-6 (FIG. 2C, Lane 3) and thrombin (FIG. 2C, lane 4) ruling out any non specific cleavage of GST by these two enzymes. GST-p53 was not cleaved on column upon incubation with caspase 6 as evidenced by absence of any stainable band in the eluate (FIG. 2D, lane 7) further confirming that the caspase 6 preparation was devoid of any non-specific protease activity.

To unequivocally confirm that the cleavage by caspase 6 occurred specifically after the aspartate in the recognition site, the inventors measured the molecular weights of purified p53 N-terminal fragment and the PDZ-like domain of SATB1 by LC ESI mass spectrometer (Bruker Daltonics). The experimental masses (12414.3 and 24596.11 Daltons respectively) were in agreement with the calculated masses (12416.8 and 24597.99 Daltons respectively) for both proteins confirming that the cleavages occurred at desired position.

TABLE 1

List of primers used

| Primer name | Nucleotide sequence | |
|---|---|---|
| Casp6-F | 5' GATCTGTTGAAATGGATG 3' | (SEQ ID NO: 13) |
| Casp6-R | 5' GATCCATCCATTTCAACA 3' | (SEQ ID NO: 14) |
| pGEX3' | 5' CCGGGAGCTGCATGTGTCAGAGG 3' | (SEQ ID NO: 15) |
| 5' BamHI-F | 5' CAACGGATCCATGGATCATTTGAAC 3' | (SEQ ID NO: 16) |
| 204 BamHI-R | 5' CCATGGATCCGTCTTTCAAATCAG 3' | (SEQ ID NO: 17) |

Advantages:

Thus, the pC6-2 novel expression vector system can be used for efficient on column removal of GST tag from the fusion proteins. The reaction is very efficient and cleavage can be performed using catalytic amounts of caspase and in as short time as 30 minutes enabling rapid purification. We have also demonstrated the utility of this system for cleavage of the GST tag from refolded GSTC6-PDZ. Additionally, the cleaved protein of interest could be obtained free of the contaminating caspase by passing it through a nickel affinity column. The availability of such vectors will facilitate expression and purification of a large number of proteins that otherwise contain internal sites for proteases typically used for removal of fusion tag.

We claim:

1. A novel expression cassette comprising an oligonucleotide encoding for a cleavage recognition site by a caspase, operably linked to a sequence encoding for a fusion protein, said fusion protein comprising a protein of interest having no internal cleavage site for caspase optionally fused to a purification tag, wherein the oligonucleotide is SEQ ID NO:13 or SEQ ID NO:14 encoding the caspase recognition site V-E-M-D (SEQ ID NO: 1) i.e. Valine-glutamic acid-methionine-aspartic acid (SEQ ID NO:1) or val-glu-met-asp (SEQ ID NO: 1) or V-E-I-D (SEQ ID NO: 2), and wherein the protein of interest is selected from the group consisting of SATB1, p53, PARP, Ikaros, cMyb, cMyc and HDAC1.

2. A cassette as claimed in claim 1 wherein the caspase is a member of the caspase family selected from caspase 6, caspase 3, caspase 7 and caspase 11.

3. A cassette as claimed in claim 1 wherein the caspase is caspase 6.

4. A cassette as claimed in claim 1 wherein the purification tag is selected from glutathione-S-transferase (GST), Hexa-histidine (His tag) (SEQ ID NO: 18), CBD (Chitin binding domain), and MBD (Maltose binding domain.

5. A cassette as claimed in claim 1 wherein the purification tag is an affinity tag used for expression in a host selected from bacteria, yeast, insect cell lines and mammalian cells.

6. A vector comprising the expression cassette as claimed in any of claims 1-3.

7. An expression system as claimed in claim 1 wherein the expression system further comprises a promoter, cloning sites, ligation sites, oligonucleotide annealing, expression of synthetic oligonucleotide encoding caspase recognition and cleavage site peptide in fusion with any tag and its use in protein purification.

8. A host cell transfected or transferred with the expression vector of claim 4, wherein the cell is selected from a bacterium or mammalian cell.

9. A kit for protein purification, comprising the expression vector of claim 6, annealed oligonucleotide encoding for VEMD (SEQ ID NO: 1) and harbouring BamHI ligatable overhanged ends, buffer used for the cleavage at caspase 6 cleavage site by caspase 6, Caspase 6 enzyme, removal process of His tagged Caspase 6 and manual of instructions.

10. A method for purifying a protein of interest comprising the steps of:
(a) providing an expression system as claimed in claim 8,
(b) transforming a host cell with the expression system,
(c) culturing the host cell under conditions whereby the fusion protein is expressed in recoverable amount,
(d) lysing the host cell to recover the protein expressed from soluble and insoluble fractions and obtaining a lysate, and
(e) purifying the protein by passing the lysate over a resin column.

* * * * *

SEQUENCE LISTING

```
<160> NUMBER OF SEQ ID NOS: 18

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Glu Met Asp
```

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Glu Ile Asp
  1

<210> SEQ ID NO 3
<211> LENGTH: 42
<212> TYPE: DNA
<213> ORGANISM: Artificial Sequence
<220> FEATURE:
<221> NAME/KEY: CDS
<222> LOCATION: (1)..(42)
<220> FEATURE:
<223> OTHER INFORMATION: Description of Artificial Sequence: Synthetic
      oligonucleotide

<400> SEQUENCE: 3 ctg gtt ccg cgt gga tcc cca gga att ccc ggg tcg act cga         42
Leu Val Pro Arg Gly Ser Pro Gly Ile Pro Gly Ser Thr Arg
  1               5                  10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Val Pro Arg Gly Ser Pro Gly Ile Pro Gly Ser Thr Arg
  1               5                  10

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctggttccgc gtg                                                  13

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatccacgcg gaaccag                                              17

<210> SEQ ID NO 7
<211> LENGTH: 29
<212> TYPE: DNA
<213> ORGANISM: Artificial Sequence
<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gatccccagg aattcccggg tcgactcga                                      29

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tcgagtcgag ccgggaattc ctggg                                          25

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gatctgttga aatggatg                                                  18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gatccatcca tttcaaca                                                  18

<210> SEQ ID NO 11
<211> LENGTH: 60
<212> TYPE: DNA
<213> ORGANISM: Artificial Sequence
<220> FEATURE:
<221> NAME/KEY: CDS
<222> LOCATION: (1)..(60)
<220> FEATURE:
<223> OTHER INFORMATION: Description of Artificial Sequence: Synthetic
      oligonucleotide

<400> SEQUENCE: 11 ctg gtt ccg cgt gga tct gtt gaa atg gat gga tcc cca gga att ccc     48
Leu Val Pro Arg Gly Ser Val Glu Met Asp Gly Ser Pro Gly Ile Pro
  1               5                  10                  15 ggg tcg act cga                                                      60
Gly Ser Thr Arg
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Leu Val Pro Arg Gly Ser Val Glu Met Asp Gly Ser Pro Gly Ile Pro
 1               5                  10                  15

Gly Ser Thr Arg
            20

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gatctgttga aatggatg                                                 18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gatccatcca tttcaaca                                                 18

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccgggagctg catgtgtcag agg                                           23

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
caacggatcc atggatcatt tgaac                                         25

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccatggatcc gtctttcaaa tcag                                          24

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
```

-continued

```
       6xHis tag

<400> SEQUENCE: 18

His His His His His His
  1               5
```